United States Patent

Borrod et al.

[11] Patent Number: 4,960,454
[45] Date of Patent: Oct. 2, 1990

[54] SULPHONYLUREA-TYPE HERBICIDES

[75] Inventors: Guy Borrod; Alain Gadras, both of Lyon, France

[73] Assignee: Rhone-Poulenc Agrochimie, Lyon, France

[21] Appl. No.: 206,740

[22] Filed: Jun. 15, 1988

[30] Foreign Application Priority Data

Jun. 25, 1987 [FR] France .................................. 8709177

[51] Int. Cl.$^5$ .................. C07D 239/69; C07D 401/12; C07D 403/12; C07D 409/12
[52] U.S. Cl. .......................................... 71/92; 71/90; 544/229
[58] Field of Search ....................... 71/92, 90; 544/229

[56] References Cited

U.S. PATENT DOCUMENTS 4,534,790  8/1985  Wolf ........................................ 71/93
4,786,734  11/1988  Hanagan ................................. 71/92

Primary Examiner—John M. Ford
Attorney, Agent, or Firm—Burns, Doane, Swecker & Mathis

[57] ABSTRACT

Herbicides of the formula (I):

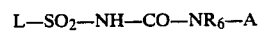

L—SO$_2$—NH—CO—NR$_6$—A in which:
L denotes one of the groups of the formulae L-1 to L-6 given below,
A denotes the group of the formula (II) given below,

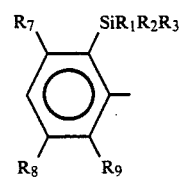

L-1

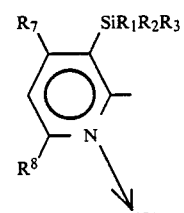

L-2

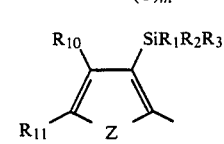

L-3

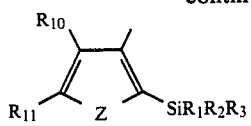

L-4

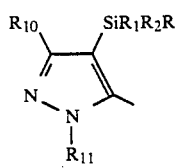

L-5

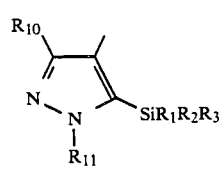

L-5

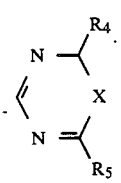

(A)

R$_1$, R$_2$ and R$_3$ can be identical or different and represent a C$_1$–C$_4$ alkyl radical or a C$_7$–C$_{11}$ aralkyl radical, especially benzyl;

R$_7$, R$_8$ and R$_9$ can be identical or different and represent a hydrogen or halogen atom, a C$_1$–C$_4$ radical which is optionally substituted by one or more halogen atoms or C$_1$–C$_4$ alkoxy or C$_1$–C$_4$ alkylthio radicals, C$_3$–C$_6$ cycloalkyl which is optionally substituted by one or more halogen atoms or C$_1$–C$_4$ alkoxy or C$_1$–C$_4$ alkylthio radicals, C$_1$–C$_4$ alkoxy or C$_1$–C$_4$ alkylthio which are optionally substituted by one or more halogen atoms or C$_1$–C$_4$ alkoxy or C$_1$–C$_4$ alkylthio radicals, R$_{13}$ S(O)$_n$—, n being an integer equal to 1 or 2 and R$_{13}$ being a C$_1$–C$_4$ alkyl radical which is optionally substituted by one or more halogen atoms or C$_1$–C$_4$ alkoxy or C$_1$–C$_4$ alkylthio radicals, COOR$_{14}$, where R$_{14}$ is a hydrogen atom, a C$_1$–C$_4$ alkyl or C$_3$–C$_6$ cycloalkyl radical which is optionally substituted by one or more halogen atoms or C$_1$–C$_4$ alkoxy or C$_1$–C$_4$ alkylthio radicals, C$_3$–C$_6$ alkenyl which is optionally substituted by one or more halogen atoms, R$_{10}$ and R$_{11}$ can be identical or different and have the same means as R$_7$, with the exception of the halogen atom. m denotes 0 or 1.

Z is the oxygen atom, the sulphur atom or the group =N—R$_{12}$.

R$_{12}$ is a C$_1$–C$_6$ alkyl, C$_6$–C$_{10}$ aryl or C$_7$–C$_{11}$ aralkyl radical, preferably methyl.

X is a trivalent radical, —CH= or —N=, preferably —N=. R$_4$ and R$_5$ are identical or different and represent a C$_1$–C$_4$ alkyl radical (preferably methyl), C$_1$–C$_4$ alkoxy radical (preferably methoxy), C$_1$–C$_4$ alkylthio radical (preferably methylthio), C$_1$–C$_4$ haloalkyl radical (preferably trifluoromethyl), C$_1$–C$_4$ haloalkoxy radical (preferably di- or trifluoromethoxy), C$_1$–C$_4$ (Abstract continued on next page.)

haloalkylthio radical (preferably trifluoromethylthio), $C_2$–$C_6$ alkoxyalkyl radical (preferably methoxymethyl, $C_2$–$C_6$ alkoxyalkoxy radical (preferably methoxymethoxy), $C_1$–$C_4$ alkylamino radical, di($C_1$–$C_4$ alkyl)amino radical or a halogen atom (preferably chlorine).

$R_6$ represents the hydrogen atom or a $C_1$–$C_4$ radical (preferably methyl), advantageously, $R_6$ is the hydrogen atom and the agriculturally acceptable salts of these compounds.

8 Claims, No Drawings

SULPHONYLUREA-TYPE HERBICIDES

The present invention relates to novel silicon-containing sulphonylureas having herbicidal activity, the preparations containing them, procedures for their preparation, and their use.

Sulphonylurea-type compounds for use as herbicides are mentioned in numerous earlier documents, of which EP-A Nos.0,030,139, 0,209,230 and 0,212,779 may be quoted.

It is an aim of the invention to provide compounds exhibiting a herbicidal activity.

Another aim of the invention is to provide compounds exhibiting a selective herbicidal activity with particular regard to cereals, maize, sugar beet, sunflower, rice, soya beans, cotton and oil seed rape.

These aims are partly or completely achieved by means of the compounds of the invention.

Formula (I) represents the formula (I) of the novel sulphonylureas according to the invention:

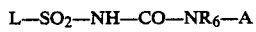

in which:
L denotes one of the groups of the formulae L-1 to L-6 given below.
A denotes the group of the formula given below.

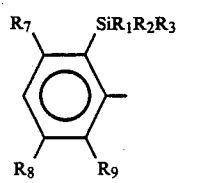   L-1

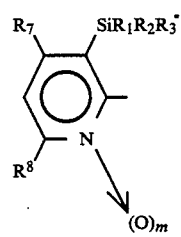   L-2

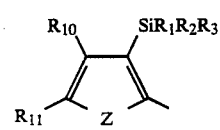   L-3

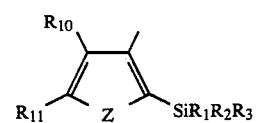   L-4

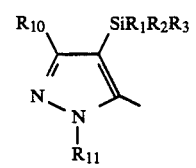   L-5

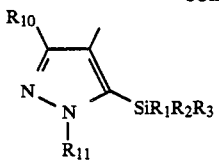   L-5

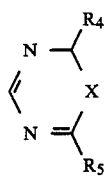   (A)

$R_1$, $R_2$ and $R_3$ can be identical or different and represent a $C_1$-$C_4$ alkyl radical or a $C_7$-$C_{11}$ aralkyl radical, especially benzyl;

$R_7$, $R_8$ and $R_9$ can be identical or different and represent a hydrogen or halogen atom, a $C_1$-$C_4$ alkyl radical which is optionally substituted by one or more halogen atoms or $C_1$-$C_4$ alkoxy or $C_1$-$C_4$ alkylthio radicals, $C_3$-$C_6$ cycloalkyl which is optionally substituted by one or more halogen atoms or $C_1$-$C_4$ alkoxy or $C_1$-$C_4$ alkylthio radicals, $C_1$-$C_4$ alkoxy or $C_1$-$C_4$alkylthio which are optionally substituted by one or more halogen atoms or $C_1$-$C_4$ alkoxy or $C_1$-$C_4$ alkylthio radicals, $R_{13}$ S(O)n—, n being an integer equal to 1 or 2 and $R_{13}$ being a $C_1$-$C_4$ alkyl radical which is optionally substituted by one or more halogen atoms or $C_1$-$C_4$ alkoxy or $C_1$-$C_4$ alkylthio radicals, $COOR_{14}$, where $R_{14}$ is a hydrogen atom, a $C_1$-$C_4$ alkyl or $C_3$-$C_6$ cycloalkyl radical which is optionally substituted by one or more halogen atoms or $C_1$-$C_4$ alkoxy or $C_1$-$C_4$ alkylthio radicals, $C_3$-$C_6$ alkenyl which is optionally substituted by one or more halogen atoms, $R_{10}$ and $R_{11}$ can be identical or different and have the same meaning as $R_7$, with the exception of the halogen atom.

m denotes 0 or 1.

Z is the oxygen atom, the sulphur atom or the group $=N$—$R_{12}$.

$R_{12}$ is a $C_1$-$C_6$ alkyl, $C_6$-$C_{10}$ aryl or $C_7$-$C_{11}$ aralkyl radical, preferably methyl.

X is a trivalent radical, —CH= or —N=, preferably —N=.

$R_4$ and $R_5$ are identical or different and represent a $C_1$-$C_4$ alkyl radical (preferably methyl), $C_1$-$C_4$ alkoxy radical (preferably methoxy), $C_1$-$C_4$ alkylthio radical (preferably methylthio), $C_1$-$C_4$ haloalkyl radical (preferably trifluoromethyl), $C_1$-$C_4$ haloalkoxy radical (preferably di- or trifluoromethoxy), $C_1$-$C_4$ haloalkylthio radical (preferably trifluoromethylthio), $C_2$-$C_6$ alkoxyalkyl radical (preferably methoxymethyl), $C_2$-$C_6$ alkoxyalkoxy radical (preferably methoxymethoxy), $C_1$-$C_4$ alkylamino radical, di($C_1$-$C_4$ alkyl)amino radical or a halogen atom (preferably chlorine).

$R_6$ represents the hydrogen atom or a $C_1$-$C_4$ alkyl radical (preferably methyl), advantageously, $R_6$ is the hydrogen atom.

The invention also comprises the agriculturally acceptable salts of these compounds. These acceptable salts are well known to those familiar with the art, especially those which are formed with mineral bases: sodium hydroxide, potassium hydroxide and alkylammonium.

In a first advantageous variant of the present invention, L denotes the group L-1.

In a second advantageous variant of the invention, the compounds of the formula (I) in which $R_1$, $R_2$ and $R_3$ are the methyl radical are chosen for their herbicidal properties.

In a third advantageous variant, on its own or in combination with one or more of the above, $R_4$ and $R_5$ are identical or different and are a halogen atom (preferably the chlorine atom), or a $C_1$-$C_4$ alkyl radical (preferably methyl) or a $C_1$-$C_4$ alkoxy radical (preferably methoxy), or a $C_1$-$C_4$ haloalkoxy radical (preferably difluoromethoxy), $C_1$-$C_4$ alkylthio, $R_{13}SO_2$, $R_{13}$ being a $C_1$-$C_4$ alkyl radical.

In a fourth advantageous variant, on its own or in combination with one or more of the above, $R_7$, $R_8$ and $R_9$ are chosen from amongst halogen atoms or hydrogen atoms or the $C_1$-$C_4$ alkoxy radicals, and $R_7$, $R_8$ and $R_9$ preferably denote the hydrogen atom.

In a fifth advantageous variant on its own or in combination with one or more of the above, $R_{10}$ and $R_{11}$ are chosen from amongst hydrogen atoms or the $C_1$-$C_4$ alkoxy radicals, and $R_{10}$ and $R_{11}$ preferably denote the hydrogen atom.

In the present description, the various formulae (I) et seq. are collated on one page which must be regarded as being an integral part of the description of the invention and not only as illustrative figures.

The silicon-containing sulphonylureas of the formula (I) can be obtained by reacting an aminopyrimidine or an aminotriazine of the formula (II) A—NHR$_6$ with a sulphonyl isocyanate of the formula (III) L—SO$_2$—NCO, preferably in a stoichiometric quantity, in an inert solvent such as chloroform, acetonitrile, toluene, xylene or chlorobenzene, at a temperature from 20° to 100° C.

The sulphonyl isocyanates of the formula (III) can be obtained by reacting phosgene with the sulphonamides of the formula (IV) L—SO$_2$—NH$_2$, preferably with an excess of phosgene (1.5 to 15 moles), in the presence of alkyl isocyanate (preferably butyl) in a proportion of 10 to 100% of the stoichiometry, and in the presence of a catalytic amount of a tertiary amine (for example, 1,4-diazabicyclo[2.2.2]octane in an inert solvent having a high boiling point, such as: xylene, chlorobenzene, dichlorobenzene and tetralin; the reaction is generally carried out at temperatures between 120° and 200° C.

In the case where $R_7$, $R_8$ and $R_9$ are other than the halogen atom, the sulphonamides of the formula (IV) can be obtained by reacting a compound of the formula (V) L—SiR$_1$R$_2$R$_3$ with sulphamoyl chloride ClSO$_2$NH$_2$, in the presence of aluminium trichloride, as described for example in Journal of Chemical Research (s), 1982, pages 16–17, P Babin et al.

The compounds of the formula (V), which are orthodi-(trialkylsilane) aryls, can be prepared by reacting the compound of the formula (VI) R—Hal, wherein R has one of the meanings of the group L, except that the group SiR$_1$R$_2$R$_3$ is replaced by the Hal radical, Hal being a bromine or chlorine atom, with trimethylsilane chloride in the presence of magnesium, as described for example in Journal of Organometallic Chemistry 84 (1975), pages 165–175, Bourgeois et al.

The compounds of the formulae (A) and (VI) are obtained in a known manner. For the compounds of the formula (A) reference is made for example to the document EP-A No.0,209,230, columns 45 and 46.

The silicon-containing sulphonylureas of the formula (I) can also be obtained by reacting a pyrimidinyl or triazinyl aryl carbamate of the formula (XII) Ph—O—CO—A, wherein Ph is an aryl ring, preferably phenyl, with a sulphonamide of the formula (IV), preferably in a stoichiometric quantity, in the presence of a tertiary amine (for example 1,8-diazabicyclo[5.4.0]undec-7-ene in an inert solvent, such as chloroform, acetonitrile, acetone, tetrahydrofuran or dioxane, at a temperature from 20° to 100° C.

The aryl carbamates of the formula (XII) can be obtained by reacting an aryl chloroformate, preferably phenyl chloroformate, with an amine of the formula (A), in the presence of an amine such as pyridine, in a polar aprotic solvent, such as tetrahydrofuran, preferably at room temperature.

Alternatively, the sulphonamides of the formula (IV) can be obtained from N-tert-butylsulphonamides (VII) L—SO$_2$—NH—C(CH$_3$)$_3$, by treating them in an acid medium, such as hydrochloric acid in methanol or trifluoroacetic acid, at room temperature.

The compounds of the formula (VII) can be obtained by an organolithium compound, preferably n-butyllithium, with the sulphonamide of the formula (VIII) Q—SO$_2$—NH—C(CH$_3$)$_3$, wherein Q has the same meaning as L except that the SiR$_1$R$_2$R$_3$ group is replaced by the hydrogen atom, in an ether-containing solvent and at −78° C. to 20° C., following a process similar to the one described in Journal of Organic Chemistry, 36 (1971), pages 1843–1845, J. G. Lombardino. The resulting dilithium intermediate is treated with trimethylsilyl chloride for 1 to 5 h at −30° C. to 20° C. to give (VII).

The sulphonamides of the formula (VIII) can be prepared from sulphonyl chlorides (IX) Q—SO$_2$—Cl and tert-butylamine, in accordance with the methods described in "The sulfonamides" H. K. Lewis and Co., LONDON, 1950, F. Hawking and J. S. Lawrence.

The sulphonyl chlorides (IX) can be obtained either by oxidizing a thiol or a sulphide of the formula (XI) Q—SH or Q—S—R$_{15}$, R$_{15}$ being a $C_1$-$C_6$ alkyl, $C_6$-$C_{10}$ aryl or $C_7$-$C_{11}$ aralkyl group, with chlorine in the presence of water and in a solvent, such as acetic acid, as described in Canadian Journal of Chemistry, 54 (1976), pages 498–499, R. F. LANGLER, or from an amine of the formula (X) Q—NH$_2$, by diazotizing it with sodium nitrite in hydrochloric acid, followed by reacting the resulting diazonium salt with sulphur dioxide in the presence of capric chloride, in acetic acid, as described in Journal of Organic Chemistry, 25 (1960), page 1824, YALE, SOWINSKI. In the case where Q denotes L-4 and R$_{10}$ and R$_{11}$ denote the hydrogen atom, the compound of the formula (IX) can be prepared from the sulphonic acid as described by A. ARCORIA et al. in Journal of Organic Chemistry, 39 (1974), pages 1689–1691.

In the various formulae (II) to (XII), the various substituents have the same meanings as in formula (I).

The various compounds of the formulae (III) to (V) are novel products which are also a part of the invention.

The invention also relates to the use, of the compounds of the formula (I), as herbicides.

The compounds of the formula (I) are mainly used in the form of a herbicidal preparation comprising one or more agriculturally acceptable excipients.

As a matter of fact, the compounds according to the invention are rarely used on their own for their practical application. Most frequently, these compounds are parts of preparations. These preparations which can be used as herbicidal agents contain, as the active substance, a compound according to the invention as described above in a mixture with solid or liquid excipients which are agriculturally acceptable and surfactants which are also agriculturally acceptable. Specific excipients which may be used are the customary inert excipients and the customary surfactants. These preparations are also part of the invention.

These preparations may also contain a variety of other components such as, for example, protecting colloids, adhesives, thickeners, thixotropic agents, penetrating agents, stabilizers, sequestering agents, and the like. More generally, the compounds used in the invention may be mixed with all solid or liquid additives corresponding to customary formulation techniques.

The application rates of the compounds used in the invention may be varied within a wide range, especially depending on the nature of the weeds to be destroyed and the usual degree of infestation, of the crops, with these weeds.

Generally, the preparations according to the invention usually contain about 0.05 to 95% (by weight) of a compound according to the invention, one or more solid or liquid excipients and, if appropriate, one or more surfactants.

In the present description, the expression "excipient" is taken to mean an organic or inorganic natural or synthetic substance with which the compound is mixed in order to facilitate its application on the plant, on seeds or on the soil. Thus, this excipient is generally inert and it must be agriculturally acceptable, in particular on the treated plant. The excipient may be solid (clays, natural or synthetic silicates, silica, resins, waxes, solid fertilizers, and the like) or liquid (water; alcohols, especially butanol, and the like).

The surfactant may be an emulsifier, dispersing agent or ionic or non-ionic wetting agent, or a mixture of these surfactants. Examples which may be mentioned are salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (especially alkyl phenols or aryl phenols), salts of sulphosuccinic acid esters, taurine derivatives (especially alkyltaurides), phosphoric esters of polycondensates of ethylene oxide with alcohols or phenol, esters of fatty acids and polyols, or sulphate, sulphonate and phosphate derivatives of the above compounds. Generally, the presence of at least one surfactant is indispensable as the compound and/or the inert excipient is/are not water-soluble, and the carrier agent of the application is water.

For their application, the compounds are thus generally present in the form of preparations. These preparations according to the invention are preparations in a variety of forms, solid or liquid.

Solid preparation forms which may be mentioned are powders for dusting (having a content of compound of up to 100%) and granules, especially those obtained by extrusion, by compression, by impregnating a granulated excipient, by granulation of a powder (the content of compound in these granules being between 0.5 and 80%, for the latter cases).

Liquid preparation forms or forms which are meant to give liquid compositions on application, which may be mentioned are flowables.

The flowables which can be applied by spraying are prepared such that a stable fluid product which does not settle is obtained (fine frinding), and they usually contain 10 to 75% of compound, 0.5 to 30% of surfactants, 0.1 to 30% of thixotropic agents, 0 to 30% of appropriate additives, such as antifoams, corrosion inhibitors, stabilizers, penetrating agents and adhesives and, as excipient, water or an organic liquid in which the active substance is scarcely soluble or insoluble: certain organic solids or mineral salts may be dissolved in the excipient in order to prevent settling, or as antifreeze for the water.

By way of example, the following is a preparation of a flowable:

Example:

compound: 500 g
polycondensate of ethylene oxide with tristyrylphenol phosphate: 50 g
polycondensate of ethylene oxide with alkylphenol: 50 g
sodium polycarboxylate: 20 g
glycol ethylene: 50 g
organopolysiloxane oil (antifoam): 1 g
polysaccharide: 1.5 g
water: 316.5 g The wettable powders (or powders for spraying) are usually prepared in a manner such that they contain 20 to 90% of compound, and they usually contain 0 to 15% of a wetting agent, 3 to 10% of a dispersing agent, and, if this should be necessary, 0 to 15% of one or more stabilizers and/or other additives, such as penetrating agents adhesives, or anti-caking agents, colorants, and the like, in addition to the solid excipient.

By way of example, the following are various preparations of wettable powders:

Example:

compound: 50%
calcium lignosulphonate (antiflocculant): 5%
isopropylnaphthalenesulphonate (anionic wetting agent): 1%
anti-caking silica: 5%
kaolin (filler): 39

Example:

compound: 80%
sodium alkylnaphthalenesulphonate: 2%
sodium lignosulphonate: 2%
anti-caking silica: 3%
kaolin: 13%

Example:

compound: 50%
sodium alkylnaphthalenesulphonate: 2%
low-viscosity methylcellulose: 2%
diatomaceous earth: 46%

Example:

compound: 90%
sodium dioctylsulphosuccinate: 0.2%
synthetic silica: 9.8%

Example:

compound: 400 g sodium lignosulphonate: 50 g
sodium dibutylnaphthalenesulphonate: 10 g
silica: 540 g Example:

compound: 250 g
isooctylphenoxy(polyoxyethylene)ethanol: 25 g
mixture of equal parts by weight of Champagne chalk and hydroxyethylcellulose: 17 g
sodium aluminosilicate: 543 g
kieselguhr: 165 g Example:

compound 100 g
mixture of sodium sulphate salts of saturated fatty acids: 30 g
condensation product of naphthalenesulphonic acid and formaldehyde: 50 g
kaolin: 820 g In order to obtain these powders for spraying or wettable powders, the actiVe substances are mixed intimately, in appropriate mixers, with the additives or the porous filler is impregnated with the compound and ground in mills or other suitable grinders. Thus, powders for spraying are obtained, the wettability and the suspension of which powders are advantageous; they can be suspended with water at any desired concentration.

The composition of dry flowables are substantially similar to that of wettable powders. They can be prepared by granulating the formulations described for the wettable powders, either by the moist way (the finely-divided compound being brought into contact with the inert filler and with a small quantity of water, for example 1 to 20%, or of an aqueous solution of dispersant or binder, followed by drying and sieving), or the dry way (compressing followed by grinding and sieving).

The following formulation is an exemplary embodiment of a dry flowable

Example:

compound: 800 g
sodium alkylnaphthalenesulphonate: 20 g
sodium methylenebis(naphthalenesulphonate): 80 g
kaolin: 100 g Instead of wettable powders, pastes may be produced. The conditions and methods of production and use of these pastes are similar to those of wettable powders or powders for spraying.

As already mentioned, the dispersions and aqueous emulsions, for example the preparations which are obtained by diluting a wettable powder according to the invention, by means of water, are encompassed in the general scope of the preparations which can be used in the present invention.

All these aqueous dispersions or emulsions or slurries can be applied to cultures for weeding in any convenient way, mainly by spraying, at application rates which are generally of the order of 50 to 500 liters of slurry per hectare.

The granules to be deposited on the soil are usually prepared in a manner such that their dimensions are between 0.1 and 2 mm, and they can be produced by compressing or impregnating. Preferably, the granules contain 1 to 95% of compound and 0 to 50% of additives, such as stabilizers, slow-release agents, binders and solvents.

Following an example of the preparation of granules, the following constituents are used Example:

compound: 50 g
propylene glycol: 25 g
linseed oil mixture: 50 g
clay (particle size: 0.3 to 0.8 mm): 910 g The present invention also relates to a method for weeding wherein an effective quantity of a compound of the formula (I) is applied to the plants which are to be destroyed.

The products and preparations according to the invention are easily applied to the vegetation and especially to the weeds to be eliminated when they have a green foliage.

Alternatively, a method of weeding which consists in applying an efficient quantity of a compound of the formula (I) to the areas or places where it is desirable to prevent growth or development of plants which have not yet emerged (pre-emergence treatment), for the compounds suitable for this application. Likewise, a procedure may be followed such that the crop is sown either before or after the treatment.

In general, the active substance is applied at application rates between 1 and 2,000 g/ha, preferably between 5 and 1,000 g/ha (generally 50 to 500 liters of slurry per hectare).

The following examples, which are in no way restricting, illustrate the invention and show how it can be put into practice:

EXAMPLE NO. 1

Preparation of
N-tert-butyl-2-(triethylsilyl)benzenesulphonamide
(product comes under formula VII).

30 g (0.14 mole) of N-tert-butylbenzenesulphonamide and 500 ml of tetrahydrofuran are introduced in a three-neck round-bottom 1,000-ml flask which is equipped with two funnels, and through which argon is passed.

200 ml of 1.6 N n-butyllithium (0.32 mole) are then introduced in one funnel. The tetrahydrofuran solution is cooled to $-30°$ C., and the n-butyllithium is then added at this temperature. The solution is clear at the beginning and turns yellow and eventually orange when the addition has ended. The mixture is allowed to warm to 0° C., maintained at 0° C. for half an hour, and then cooled again to $-20°$ C. In the second funnel, 50 ml (0.3 mole) of triethylsilyl chloride are introduced and added dropwise at 20° C. to the previously formed salt. The mixture is allowed to come to room temperature and is then hydrolysed with 30 ml of a 6N hydrochloric acid solution. The solution is then washed to neutrality with 300 ml of a saturated ammonium chloride solution, dried over magnesium sulphate and concentrated. 38 g of a solid in the form of a paste is obtained, which is recrystallized from 70 ml of heptane. N-tert-butyltriethyl-2-(silyl)benzenesulphonamide is obtained in the form of a white powder, melting point 98.6° C.

Mass collected: 35 g. Yield: 76%.

TABLE (I)

Compounds of the formula (VII) in which $R_8$, $R_{10}$ and $R_{11}$ stand for the hydrogen atom, which are prepared in accordance with Example 1

| Ex. | Group | $SiR_1R_2R_3$ | $R_7$ | $R_9$ | Z | m | Melting point in °C. |
|---|---|---|---|---|---|---|---|
| 1 | L-1 | $SiEt_3$ | H | H | — | — | 98.6 |

TABLE (I)-continued

Compounds of the formula (VII) in which $R_8$, $R_{10}$ and $R_{11}$ stand for the hydrogen atom, which are prepared in accordance with Example 1

| Ex. | Group | $SiR_1R_2R_3$ | $R_7$ | $R_9$ | Z | m | Melting point in °C. |
|---|---|---|---|---|---|---|---|
| 2 | L-1 | $SiMe_3$ | H | H | — | — | 100.7 |
| 3 | L-1 | $SiMe_3$ | Cl | H | — | — | 152 |
| 4 | L-1 | $SiMe_3$ | H | $CF_3$ | — | — | 144 |
| 5 | L-1 | $SiMe_3$ | H | OMe | — | — | 152 |
| 6 | L-1 | $SiMe_3$ | H | Cl | — | — | 158.3 |
| 7 | L-1 | $SiMe_3$ | H | F | — | — | 139.5 |
| 8 | L-1 | $SiMe_3$ | H | $SO_2Me$ | — | — | 136.5 |
| 9 | L-2 | $SiMe_3$ | H | — | — | 0 | 124.4 |
| 10 | L-4 | $SiMe_3$ | — | — | S | — | 120.4 |

EXAMPLE NO. 11

Preparation of 2-(triethylsilyl)benzenesulphonamide (The product comes under the formula IV).

16.5 g (50 mmol) of N-tert-butyl-2-(triethylsilyl)benzenesulphonamide are dissolved in 80 ml of trifluoroacetic acid in a one-neck round-bottom 250-ml flask. The mixture is maintained at room temperature for 2 h, with stirring.

The trifluoroacetic acid is then removed in vacuo, and the resulting residue is taken up in 60 ml of heptane.

2-(Triethylsilyl)benzenesulphonamide is obtained in the form of white crystals, melting point 85.6° C.

Mass collected: 11.9 g. Yield: 88%.

TABLE (II)

Compounds of the formula (IV) in which $R_8$, $R_{10}$ and $R_{11}$ represent the hydrogen atom, prepared according to Example 11

| Ex. | Group | $SiR_1R_2R_3$ | $R_7$ | $R_9$ | Z | m | Melting point in °C. |
|---|---|---|---|---|---|---|---|
| 11 | L-1 | $SiEt_3$ | H | H | — | — | 85.6 |
| 12 | L-1 | $SiMe_3$ | H | H | — | — | 160.7 |
| 13 | L-1 | $SiMe_3$ | Cl | H | — | — | 162 |
| 14 | L-1 | $SiMe_3$ | H | $CF_3$ | — | — | 122 |
| 15 | L-1 | $SiMe_3$ | H | OMe | — | — | 82 |
| 16 | L-1 | $SiMe_3$ | H | Cl | — | — | 80.8 |
| 17 | L-1 | $SiMe_3$ | H | F | — | — | 89 |
| 18 | L-1 | $SiMe_3$ | H | SMe | — | — | 144 |
| 19 | L-1 | $SiMe_3$ | H | $SO_2Me$ | — | — | 137.1 |
| 20 | L-2 | $SiMe_3$ | H | — | — | 0 | 127.1 |
| 21 | L-2 | $SiMe_3$ | H | — | — | 1 | 231.7 |
| 22 | L-4 | $SiMe_3$ | — | — | S | — | 124.3 |

EXAMPLE 23

Preparation of N-(4,6-dimethoxy-2-pyrimidinyl)aminocarbonyl-2-(triethylsilyl)benzenesulphonamide. (The product comes under the formula I).

1.97 g (7.26 mmol) of 2-triethylsilylbenzenesulphonamide and 2 g (7.26 mmol) of phenyl N-(4,6-dimethoxy1,3-pyrimidin-2-yl)carbamate in 35 ml of dry acetonitrile are introduced in a 100-ml round-bottom flask. 1.1 g (7.26 mmol) of 1,8-diazabicyclo[5.4.0]undec-7-ene, dissolved in 8 ml of acetonitrile, are added to the previous solution, at room temperature.

The temperature is raised by 3° to 4° C. The reaction mixture is allowed to stand for 4 h at room temperature, with stirring. 6 ml of a 10% strength hydrochloride acid solution are then added.

A white precipitate which is formed rapidly is filtered off, washed with 15 ml of diisopropyl ether and then dried in vacuo.

N-(4,6-Dimethoxy-2-pyrimidinyl)aminocarbonyl-2(triethylsilyl)benzenesulphonamide is obtained in the form of a white powder, melting point 136.5° C.

Mass collected: 2.3 g. Yield: 70%.

TABLE (III)

Compounds of the formula I in which $R_7$, $R_{10}$ and $R_{11}$ denotes the hydrogen atom, prepared in accordance with Example 23

| Ex. | Group | $SiR_1R_2R_3$ | $R_8$ | $R_9$ | Z | m | $R_4$ | $R_5$ | X | Melting point in °C. |
|---|---|---|---|---|---|---|---|---|---|---|
| 23 | L-1 | $SiEt_3$ | H | H | 13 | 13 | OMe | OMe | CH | 136.5 |
| 24 | L-1 | $SiMe_3$ | H | H | — | — | OMe | OMe | CH | 169.9 |
| 25 | L-1 | $SiMe_3$ | H | H | — | — | Me | Me | CH | 190.4 |
| 26 | L-1 | $SiMe_3$ | H | H | — | — | OMe | Me | N | 166.1 |
| 27 | L-1 | $SiMe_3$ | H | H | — | — | OMe | Me | CH | 168.1 |
| 28 | L-1 | $SiEt_3$ | H | H | — | — | OMe | OMe | N | 174.4 |
| 29 | L-1 | $SiMe_3$ | H | H | — | — | OMe | Me | N | 169.2 |
| 30 | L-1 | $SiMe_3$ | H | H | — | — | Me | Me | CH | 192.6 |
| 31 | L-1 | $SiEt_3$ | H | H | — | — | OMe | Me | CH | 156.3 |
| 32 | L-1 | $SiMe_3$ | H | Cl | — | — | OMe | OMe | CH | 179 |
| 33 | L-1 | $SiMe_3$ | H | Cl | — | — | Me | Me | CH | 198 |
| 34 | L-1 | $SiMe_3$ | H | Cl | — | — | OMe | Me | N | 200 |
| 35 | L-1 | $SiMe_3$ | H | Cl | — | — | OMe | OMe | N | 202 |
| 36 | L-1 | $SiMe_3$ | H | $CF_3$ | — | — | Me | Me | CH | 210 |
| 37 | L-1 | $SiMe_3$ | H | $CF_3$ | — | — | OMe | OMe | CH | 164 |
| 38 | L-1 | $SiMe_3$ | H | $CF_3$ | — | — | OMe | OMe | N | 160 |
| 39 | L-1 | $SiMe_3$ | H | $CF_3$ | — | — | OMe | Me | CH | 177 |
| 40 | L-1 | $SiMe_3$ | H | $CF_3$ | — | — | OMe | Me | CH | 164 |
| 41 | L-1 | $SiMe_3$ | H | F | — | — | Me | Me | CH | 184 |
| 42 | L-1 | $SiMe_3$ | H | F | — | — | OMe | OMe | CH | 157 |
| 43 | L-1 | $SiMe_3$ | H | F | — | — | OMe | Me | CH | 188 |
| 44 | L-1 | $SiMe_3$ | H | F | — | — | OMe | Me | N | 188.5 |
| 45 | L-1 | $SiMe_3$ | H | F | — | — | OMe | OMe | N | 179 |
| 46 | L-1 | $SiMe_3$ | H | F | — | — | OMe | Cl | CH | 172 |
| 47 | L-1 | $SiMe_3$ | H | OMe | — | — | OMe | OMe | CH | 130.1 |
| 48 | L-1 | $SiMe_3$ | H | SMe | — | — | Me | Me | CH | 157.3 |
| 49 | L-1 | $SiMe_3$ | H | SMe | — | — | OMe | OMe | CH | 134.3 |

TABLE (III)-continued

Compounds of the formula I in which $R_7$, $R_{10}$ and $R_{11}$ denotes the hydrogen atom, prepared in accordance with Example 23

| Ex. | Group | SiR₁R₂R₃ | $R_8$ | $R_9$ | Z | m | $R_4$ | $R_5$ | X | Melting point in °C. |
|---|---|---|---|---|---|---|---|---|---|---|
| 50 | L-1 | SiMe₃ | H | SMe | — | — | OMe | Me | N | 156.5 |
| 51 | L-1 | SiMe₃ | H | SO₂Me | — | — | OMe | OMe | CH | 109.8 |
| 52 | L-1 | SiMe₃ | H | SO₂Me | — | — | Me | Me | CH | 195.8 |
| 53 | L-1 | SiMe₃ | H | SO₂Me | — | — | OMe | OMe | N | 169.8 |
| 54 | L-1 | SiMe₃ | H | SO₂Me | — | — | OMe | Me | N | 175.5 |
| 55 | L-2 | SiMe₃ | H | — | — | 0 | Me | Me | CH | 179 |
| 56 | L-2 | SiMe₃ | H | — | — | 0 | OMe | OMe | CH | 165 |
| 57 | L-2 | SiMe₃ | H | — | — | 0 | OMe | Me | CH | 181 |
| 58 | L-2 | SiMe₃ | H | — | — | 0 | OMe | Me | N | 160 |
| 59 | L-2 | SiMe₃ | OMe | — | — | 0 | OMe | OMe | CH | 156.1 |
| 60 | L-2 | SiMe₃ | H | — | — | 1 | OMe | Me | CH | 180.3 |
| 61 | L-2 | SiMe₃ | H | — | — | 1 | Me | Me | CH | |
| 62 | L-2 | SiMe₃ | | — | — | 1 | OMe | OMe | N | 159.4 |
| 63 | L-2 | SiMe₃ | | — | — | 1 | OMe | OMe | CH | 150.7 |
| 64 | L-4 | SiMe₃ | — | — | S | — | OMe | OMe | CH | 166.9 |
| 65 | L-4 | SiMe₃ | — | — | S | — | Me | Me | CH | 190.2 |
| 66 | L-4 | SiMe₃ | — | — | S | — | OMe | Me | N | 156.3 |
| 67 | L-4 | SiMe₃ | — | — | S | — | OMe | OMe | N | 155.3 |
| 68 | L-4 | SiMe₃ | — | — | S | — | OMe | Cl | CH | 167.1 |

EXAMPLE A

Herbicidal application as a pre-emergence treatment of plant species

A certain number of seeds depending on the plant species and on the size of the seeds are sown in 7×7×8 cm pots containing light agricultural soil.

The pots are sprayed with slurry in an amount which corresponds to an application rate of 500 l/ha and which contains the active substance in the desired concentration.

Thus, treatment with the slurry is carried out on seeds which are not covered with soil (the expression slurry is used for generally describing water-diluted preparations which are applied to the plants).

The slurry used in this treatment is a solution or suspension of the active substance in an acetone/water mixture in the ratio 50/50, in the presence of 0.05% by weight of Cemulsol NP 10 (surfactant), comprising a polycondensate of ethylene oxide with an alkyl phenol (especially a polycondensate of ethylene oxide with nonylphenol) and 0.04% by weight of tween 20 (surfactant containing an oleate which is a polyoxyethylene derivative of sorbitol).

In the case of a suspension, it is obtained by mixing and grinding the ingredients in a grinder in a manner such that a medium particle size of less than 40 microns is achieved.

Various concentrations of active substance of the slurry have been used, corresponding to various rates of applied active substance. Results are given for the following application rates:

Example Nos. 38, 39 to 250 g/ha.
Example Nos. 34 to 500 g/ha.
Examples Nos. 27, 28, 32, 33, 35, 36, 55, 56, 57, 58 to 1,000 g/ha.

After the treatment, the seeds are covered with a layer of soil of about 3 mm in thickness.

The pots are then placed in containers into which the water for watering is poured, the pots are watered from beneath, and maintained for 24 days at room temperature at 70% atmospheric humidity.

After 24 days, the number of living plants in the pots which have been treated with the slurry containing the active substance to be tested, are counted, and the number of living plants in a control pot treated in the same way but with a slurry which does not contain active substance, are counted. In this manner, the percentage of destroyed treated plants is determined by comparison with a non-treated control (first line of the results). A destruction percentage of 100% means that complete destruction of the plant species in question has taken place, and a percentage of 0% means that the number of living plants in the treated pot is identical to that in the control pot. Likewise, the percentage of reduced height of undestroyed or partially destroyed species is determined (second line of results).

The results obtained are presented after Example B.

EXAMPLE B

Herbicidal application as post-emergence treatment of plant species.

A certain number of seeds, depending on the plant species and the size of the seeds, are sown in 7×7×8 cm pots containing light agricultural soil.

The seeds are then covered with a layer of soil of approximately 3 mm in thickness, and the seeds are allowed to germinate until a plantlet in a suitable stage is formed. For grasses, the stage where the second leaf is being formed is the treatment stage. For dicotyledon plants, the stage where the cotyledons are fully grown and the first true leaf is formed is the treatment stage.

The pots are then treated by spraying them with slurry in an amount corresponding to an application rate of 500 l/ha, and containing the active substance in the desired concentration.

The slurry has been prepared in the same way as in Example A.

Various concentrations of active substance of the slurry have been used which correspond to various rates of applied active substance. Results are given for the following application rates:

Example Nos. 38, 39 to 250 g/ha.
Example Nos. 34 to 500 g/ha.
Example Nos. 27, 28, 32, 33, 35, 36, 55, 56, 57, 58 to 1,000 g/ha.

The treated pots are then placed in containers into which the water for watering is poured, the pots are watered from beneath, and maintained for 24 days at room temperature at 70% atmospheric humidity.

After 24 days, the number of living plants in the pots which have been treated with the slurry containing the active substance to be tested are counted, and the number of living plants in a control pot treated in the same way but with a slurry which does not contain active substance, are counted. In this manner, the percentage of destroyed treated plants is determined by comparison with a non-treated control (first line of the results). A destruction percentage of 100% means that complete destruction of the plant species in question has taken place, and a percentage of 0% means that the number of living plants in the treated pot is identical to that in the control pot. Likewise, the percentage of reduced height of undestroyed—or partially destroyed species is determined (second line of results).

The plant species which have been used in Examples A and B are the following:

| Abbreviations | Latin name | English name |
|---|---|---|
| AVE | *Avena fatua* | wild oat |
| ECH | *Echinochloa crusgalli* | barnyard grass |
| LOL | *Lolium multiflorum* | Italian ryegrass |
| CYP | *Cyperus esculentus* | earth almond |
| CEN | *Centaurea cyanus* | cornflower |
| IPO | *Ipomea purpurea* | common morning-glory |
| SIN | *Sinapis alba* | mustard |
| ABU | *Abutilon theophrasti* | Indian mallow |
| DAU | *Daucus carota* | carrot |

The results which have been obtained in the pre-emergence treatment (application method of Example A) are listed below:

| EX | ECH | LOL | CYP | CEN | IPO | SIN | ABU | DAU |
|---|---|---|---|---|---|---|---|---|
| 27 | 50 | 100 | 30 | 50 | 0 | 90 | 0 | 0 |
|    | 50 |     | 30 | 70 | 50 |    | 70 | 50 |
| 28 |    | 0   |    | 0  | 0  | 100 | 0  | 0 |
|    |    | 30  |    | 30 | 20 |    | 20 | 50 |
| 32 | 30 | 80  | 100 | 0  | 20 | 98 | 0  | 30 |
|    | 30 |     |     | 10 | 30 |    | 30 | 40 |
| 34 | 100 | 100 | 100 | 30 | 0 | 80 | 0 | 0 |
|    |     |     |     | 70 | 0 |    | 50 | 40 |
| 35 | 100 | 100 | 100 |    |   | 100 | 100 | 90 |
| 36 | 100 | 100 | 70  |    | 0 | 30 |    |    |
|    |     |     | 20  |    | 40 | 50 |   |   |
| 38 | 30  | 98  | 80  |    | 0 | 80 | 30 |   |
|    | 60  | 0   | 0   |    | 60 | 0  | 20 |   |
| 39 | 100 | 100 | 80  |    | 0 | 80 | 0  |   |
|    |     |     |     |    | 70 |    | 30 |   |
| 55 | 10  | 0   | 30  |    |    | 30 | 20 |   |
|    | 70  | 70  | 0   |    |    | 70 | 20 |   |
| 56 | 80  | 100 | 100 |    | 0 | 98 | 30 |   |
|    |     |     |     |    | 70 |    | 30 |   |
| 57 | 80  | 98  | 80  |    | 80 | 40 | 80 |   |
|    |     |     |     |    |    | 80 |    |   |
| 58 | 50  | 100 | 30  |    | 80 | 100 | 30 |   |
|    | 80  |     | 30  |    |    |     | 0  |   |

The results obtained in the post-emergence treatment (application method of Example B) are listed below:

| EX | ECH | LOL | CYP | CEN | IPO | SIN | ABU | DAU |
|---|---|---|---|---|---|---|---|---|
| 27 | 0  | 95  | 0  | 0  | 0  | 100 | 0  | 50 |
|    | 60 |     | 30 | 30 | 50 |    | 50 | 50 |
| 28 |    | 30  |    |    | 0  | 100 | 0  | 0 |
|    |    | 50  |    |    | 50 |    | 30 | 30 |
| 32 | 80 | 0   | 0  | 0  | 0  | 100 | 80 | 100 |
|    |    | 50  | 30 | 50 | 40 |    |    |    |
| 33 | 20 |     |    |    | 0  | 100 | 0  |   |
|    | 80 |     |    |    | 20 |    | 20 |   |
| 34 | 100 | 95 | 30 | 0  | 0  | 100 | 80 | 50 |
|    |     |    | 50 | 30 | 70 |    |    | 50 |
| 35 | 80  | 100 | 0 |    | 100 | 100 | 100 | 80 |
|    |     |     | 50 |   |    |    |    |   |
| 36 | 30  | 10  | 0  | 0  | 20 | 100 | 20 |   |
|    | 80  | 70  | 40 | 0  | 60 |    | 50 |   |
| 38 | 30  | 10  | 0  |    | 100 | 100 | 0  |   |
|    | 70  | 60  | 60 |    |    |    | 30 |   |
| 39 | 20  | 50  | 0  |    | 100 | 100 | 20 |   |
|    | 70  | 70  | 30 |    |    |    | 60 |   |
| 55 |     |     |    |    |    | 30 | 80 |   |
|    |     |     |    |    |    | 30 |    |   |
| 56 | 100 | 30  | 0  |    | 100 | 100 | 20 |   |
|    |     | 70  | 60 |    |    |    | 40 |   |
| 57 | 80  | 80  | 0  |    | 70 | 100 | 0  |   |
|    |     |     | 20 |    | 70 |    | 30 |   |
| 58 | 90  | 100 |    |    | 100 | 100 |    |   |

The trials which have been carried out clearly show the advantageous properties of the compounds according to the invention, both for pre-emergence treatments of the crops and for post-emergence treatments, both on monocotyledon (grasses) and dicotyledon wild-growing species.

We claim:

1. A compound containing a sulphonylurea group selected from the compounds of the formula:

$$L-SO_2-NH-CO-NR_6-A \qquad (I)$$

in which:

L represents one of the groups of the formulae L-1 to L-6 given below, A represents the group of the formula given below,

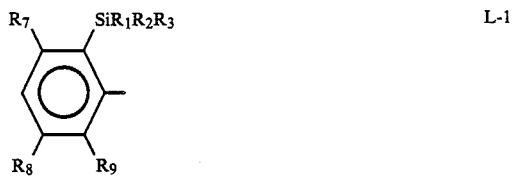

L-1

L-2

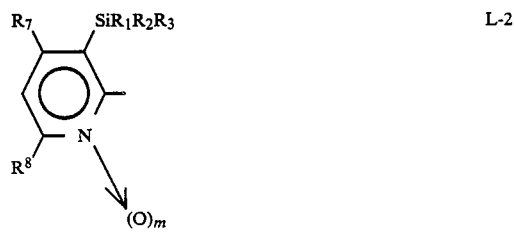

L-3

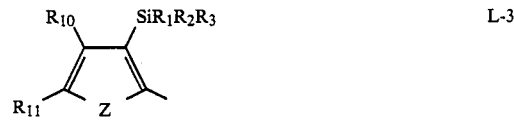

L-4

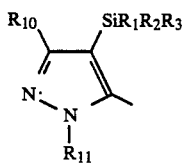
L-5

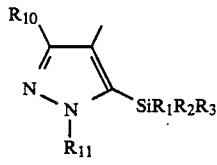
L-5

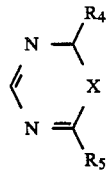
(A)

$R_1$, $R_2$ and $R_3$ can be identical or different and represent a $C_1$–$C_4$ alkyl radical or a $C_7$–$C_{11}$ alkyl radical which is unsubstituted or substituted by one or more halogen atoms or $C_1$–$C_4$ alkoxy or $C_1$–$C_4$ alkylthio radicals, $C_3$–$C_6$ cycloalkyl which is unsubstituted or substituted by one or more halogen atoms or $C_1$–$C_4$ alkoxy or $C_1$–$C_4$ alkylthio radicals, $C_1$–$C_4$ alkoxy or $C_1$–$C_4$ alkylthio which are unsubstituted or substituted by one or more halogen atoms or $C_1$–$C_4$ alkoxy or $C_1$–$C_4$ alkylthio radicals, $R_{13}S(O)_n$—, n being an integer equal to 1 or 2 and $R_{13}$ being a $C_1$–$C_4$ alkyl radical which is unsubstituted or substituted by one or more halogen atoms or $C_1$–$C_4$ alkoxy or $C_1$–$C_4$ alkylthio radicals, $COOR_{14}$, where $R_{14}$ is a hydrogen atom, a $C_1$–$C_4$ alkyl or $C_3$–$C_6$ cycloalkyl radical which is unsubstituted or substituted by one or more halogen atoms or $C_1$–$C_4$ alkoxy or $C_1$–$C_4$ alkylthio radicals, $C_3$–$C_6$ alkenyl which is unsubstituted or substituted by one or more halogen atoms;

$R_{10}$ and $R_{11}$ can be identical or different and have the same meaning as $R_7$, with the exception of the halogen atom;

m is 0 or 1;

Z is the oxygen atom, the sulphur atom or the group $=N$—$R_{12}$, wherein $R_{12}$ is a $C_1$–$C_6$ alkyl, $C_6$–$C_{10}$ aryl or $C_7$–$C_{11}$ aralkyl radical;

X is a trivalent radical, —CH=;

$R_4$ and $R_5$ are identical or different and represent a $C_1$–$C_4$ alkyl radical, $C_1$–$C_4$ alkoxy radical, $C_1$–$C_4$ alkylthio radical, $C_1$–$C_4$ haloalkyl radical, $C_1$–$C_4$ haloalkoxy radical, $C_1$–$C_4$ haloalkylthio radical, $C_2$–$C_6$ alkoxyalkyl radical, $C_2$–$C_6$ alkoxyalkoxy radical, $C_1$–$C_4$ alkylamino radical, di($C_1$–$C_4$ alkyl)amino radical or a halogen atom;

$R_6$ represents the hydrogen atom or a $C_1$–$C_4$ alkyl radical, or an agriculturally acceptable salt of these compounds.

2. The compound according to claim 1, wherein the L group represents L-1.

3. The compound according to claim 1 or 2, wherein $R_1$, $R_2$ and $R_3$ are the methyl radical.

4. The compound according to claim 1, wherein $R_4$ and $R_5$ are identical or different and are selected from the group consisting of a halogen atom, a $C_1$–$C_4$ alkyl radical, a $C_1$–$C_4$ alkoxy radical and a $C_1$–$C_4$ haloalkoxy radical.

5. The compound according to claim 1, wherein $R_7$, $R_8$ and $R_9$ are selected from the group consisting of halogen atoms, hydrogen atoms, and $C_1$–$C_4$ alkoxy radicals.

6. The compound according to claim 1, wherein $R_{10}$ and $R_{11}$ are hydrogen atoms or the $C_1$–$C_4$ alkoxy radicals.

7. A herbicidal composition comprising an herbicidally effective amount of a compound according to claim 1 together with an inert agriculturally acceptable excipient.

8. The composition according to claim 7, which contains 0.05 to 95% of a compound as defined in claim 1.

* * * * *

UNITED STATES PATENT AND TRADEMARK OFFICE
CERTIFICATE OF CORRECTION

PATENT NO.   : 4,960,454

DATED        : October 2, 1990

INVENTOR(S)  : Guy Borrod; Alain Gadras

It is certified that error appears in the above-identified patent and that said Letters Patent is hereby corrected as shown below:

Title page, ABSTRACT, line 23 after the formula, please rewrite "means" as --meaning--; Column 3, line 67, please delete "(A)" and substitute --(II)--; Column 4, line 1, please delete "(A)" and substitute --(II)--; Column 4, line 16, please delete "(A)" and substitute --(II)--; Column 4, line 25, after "by" and before "an", please insert --reacting--; Column 4, line 51, please rewrite "capric" as --cupric--; Column 5, line 27, please delete "usually"; Column 7, lines 39-40, please delete "exemplary embodiment" and substitute --example-- therefor; and Column 10, line 31, please rewrite "hydrochloride" as --hydrochloric--.

Signed and Sealed this

Fifth Day of May, 1992

Attest:

DOUGLAS B. COMER

*Attesting Officer*          *Acting Commissioner of Patents and Trademarks*

UNITED STATES PATENT AND TRADEMARK OFFICE
CERTIFICATE OF CORRECTION

PATENT NO. : 4,960,454
DATED : October 2, 1990
INVENTOR(S) : BORROD ET AL.

It is certified that error appears in the above-identified patent and that said Letters Patent is hereby corrected as shown below:

IN THE CLAIMS

In Claim 1, At Column 15, line 25, amend "$C_7$-$C_{11}$ alkyl radical" to
--$C_7$-$C_{11}$ aralkyl radical;
$R_7$, $R_8$ and $R_9$ can be identical or different and represent a hydrogen or halogen atom, a $C_1$-$C_4$ alkyl radical--.

Signed and Sealed this

Eighteenth Day of January, 1994

Attest:

BRUCE LEHMAN

Attesting Officer       Commissioner of Patents and Trademarks